US006037162A

United States Patent [19]

Raveh

[11] Patent Number: 6,037,162

[45] Date of Patent: Mar. 14, 2000

[54] DNA SEGMENTS ENCODING A DOMAIN OF HO-ENDONUCLEASE

[75] Inventor: Dina Raveh, Negev, Israel

[73] Assignee: Ben Gurion University, Beer Sheva, Israel

[21] Appl. No.: 09/171,304

[22] PCT Filed: Feb. 15, 1998

[86] PCT No.: PCT/IL98/00076

§ 371 Date: Jan. 11, 1999

§ 102(e) Date: Jan. 11, 1999

[87] PCT Pub. No.: WO98/36079

PCT Pub. Date: Aug. 20, 1998

[30] Foreign Application Priority Data

Feb. 17, 1997 [IL] Israel ........................................ 120241

[51] Int. Cl.[7] ............................ C12N 9/22; C12N 15/55; C12N 15/62

[52] U.S. Cl. ........................ 435/199; 536/23.2; 536/23.4; 435/69.7

[58] Field of Search .................................. 435/199, 69.7; 536/23.2, 23.4

[56] References Cited

FOREIGN PATENT DOCUMENTS

96/40882 12/1996 WIPO .

OTHER PUBLICATIONS

Nahon, E., et al. (1998) Nucl. Acid Res. 26(5), 1233–1239.

Meiron, H., et al. (1995) Curr. Genet. 28, 367–373.

Dohrmann, P.R., et al. (1992) Genes and Dev. 6(1), 93–104.

Gimble, F. S., et al. (1995) J. Biol. Chem. 270(11), 5849–5856.

*Primary Examiner*—Charles L. Patterson, Jr.
*Attorney, Agent, or Firm*—Townsend & Townsend & Crew

[57] ABSTRACT

The invention provides an isolated DNA segment encoding a domain of HO-endonuclease, said segment being selected from the group consisting of an isolated DNA segment encoding the N-terminus of HO-endonuclease which contains the sequence-specific catalytic nuclease activity of said HO-endonuclease, said DNA fragment comprising at least 755 nt and encoding for at least 251 amino acids, and said endonuclease being characterized by the presence of at least one copy of the dodecapeptide motif LAGLI-DADG (SEQ ID NO:1) and an isolated DNA segment encoding the C-terminus of HO-endonuclease which contains the DNA binding/recognition activity of said HO-endonuclease, said C-terminus comprising 360 nt and encoding for 120 amino acids.

16 Claims, 4 Drawing Sheets

Cleavage by H0-Swi5 chimera of URS1

Fig.6A.

PRIMERS USED FOR MAKING THE HO-SWI5 CHIMERIC ENDONUCLEASE
SWI5 ZINC FINGER PRIMERS

NDEFWRD BAM SITE
ATG ACA AAT GGA TCC TCA AAA ATC ACA AG
NDEREV HIND3 SITE
CCG CTG CAA AGC TTT CCTA CTT CTG TGC

Fig.6B.

PRIMERS USED FOR SUBCLONING THE HO-SWI5 CHIMERIC ENDONUCLEASE INTO THE HISTIDINE-TAGGED BACTERIAL VECTOR AND INTO THE YEAST EXPRESSION VECTOR.
HO-SWI5 CHIMERA PRIMERS

HOSWF NDE SITE STARTS NEAR PST1 SITE
CTG CAG CAA TGT CAT ATG CTT GAT GGT AGG
HOSWB BAM SITE done on DNA with Hind3 site
CGG GAT CCG CTG CAA AGC ATT CTA CTT CTG

DNA SEGMENTS ENCODING A DOMAIN OF HO-ENDONUCLEASE

FIELD OF THE INVENTION

The present invention relates to DNA segments encoding the two functional domains of HO-endonuclease, the catalytic and DNA recognition domains.

BACKGROUND ART

HO-endonuclease belongs to the dodecapeptide family of endonucleases that cleave a large, unique (>18 bp) DNA recognition sequence that lacks dyad symmetry. These nucleases are encoded by nuclear or mitochondrial and chloroplast group I intron genes, or exist as inteins having their coding sequences embedded in-frame within unrelated genes that undergo protein splicing, such that two proteins are generated from a single translation product. Dodecapeptide endonucleases are known in phylogenetically diverse species, and new genes are constantly being discovered.

HO-endonuclease of the yeast *Saccaromyces cerevisiae* initiates a mating type switch by making a site-specific double strand break in the mating type gene MAT, and attains site-specificity by virtue of a large (18–24 bp) target site. It has now been shown that a 113-residue N-terminal truncation of HO-endonuclease is able to cleave its cognate site and to initiate a mating type switch in yeast.

HO is the only dodecapeptide endonuclease with a zinc finger DNA-binding domain. The present inventors have cloned an inactive allele of HO-endonuclease from a laboratory strain of yeast [Meiron, et al., "Identification of the Heterothallic Mutation in HO-endonuclease of *S. cerevisiae* Using HO/ho Chimeric Genes," *Curr. Genet.,* Vol. 28, pp. 367–373 (1995)]. In that study, chimeric genes were made between the active and inactive endonuclease genes and tested for their activity in yeast. It was found that of the four amino acid substitutions in the mutant (ho) gene, only one substitution affected endonucleolytic activity. This mutation is in the first zinc finger of HO.

In the present invention, it is shown that it is possible to target endonucleolytic activity to a different site by exchange of the zinc finger domain of HO for that of the yeast transcription factor Swi5. It was found that a chimeric endonuclease comprising the nuclease domain of HO and the zinc finger domain of Swi5 cleaves the Swi5 target site URS1. This shows that it is possible to target the catalytic domain of dodecapeptide endonucleases via various DNA-binding moieties, and that they present a general nuclease domain in the design of highly site-specific targeted endonucleases.

SUMMARY OF THE INVENTION

Accordingly, it is an object of the present invention to provide isolated domains of dodecapeptide endonucleases, in particular of HO-endonuclease, for chimeric nucleases that will be used as rare cutters in vitro for mapping and sequencing and in vivo for gene therapy and against pathogenic agents.

The present invention achieves the above objective by providing an isolated DNA segment encoding a domain of HO-endonuclease, said segment being selected from the group consisting of (a) an isolated DNA segment encoding the N-terminus of HO-endonuclease which contains the general catalytic nuclease activity of said HO-endonuclease, said DNA segment comprising at least 755 nt and encoding for at least 251 amino acids, and said endonuclease being characterized by the presence of at least one copy of the dodecapeptide motif LAGLI-DAIG; (SEQ ID NO:1) and (b) an isolated DNA segment encoding the C-terminus of HO-endonuclease which contains the DNA binding/recognition activity of said HO-endonuclease, said C-terminus comprising about 360 nt and encoding for about 120 amino acids.

In another aspect of the invention, there is provided a DNA construct comprising a DNA segment encoding the catalytic nuclease domain of a dodecapeptide endonuclease, a second DNA segment encoding a DNA binding moiety and a vector, said endonuclease being characterized by the presence of at least one copy of the dodecapeptide motif LAGLI-DADG (SEQ ID No:1)

In another aspect of the invention, there is provided a chimeric restriction endonuclease, comprising the catalytic nuclease domain of a dodecapeptide endonuclease linked to a recognition domain of a different DNA binding protein, said endonuclease being characterized by the presence of at least one copy of the dodecapeptide motif LAGLI-DADG (SEQ ID NO:1).

A further aspect of the invention provides a chimeric restriction endonuclease comprising the catalytic nuclease domain of HO-endonuclease linked to a synthetic polypeptide designed to recognize a specific DNA target sequence.

A yet further aspect of the invention provides the use of the catalytic domain of a member of the dodecapeptide family of endonucleases as an effector domain in the generation of targeted endonucleases, substantially as described herein, said endonucleases being characterized by the presence of at least one copy of the dodecapeptide motif LAGLI-DADG (SEQ ID NO:1).

BRIEF DESCRIPTION OF THE DRAWINGS

The invention will now be described in connection with certain preferred embodiments with reference to the following illustrative figures and examples, so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
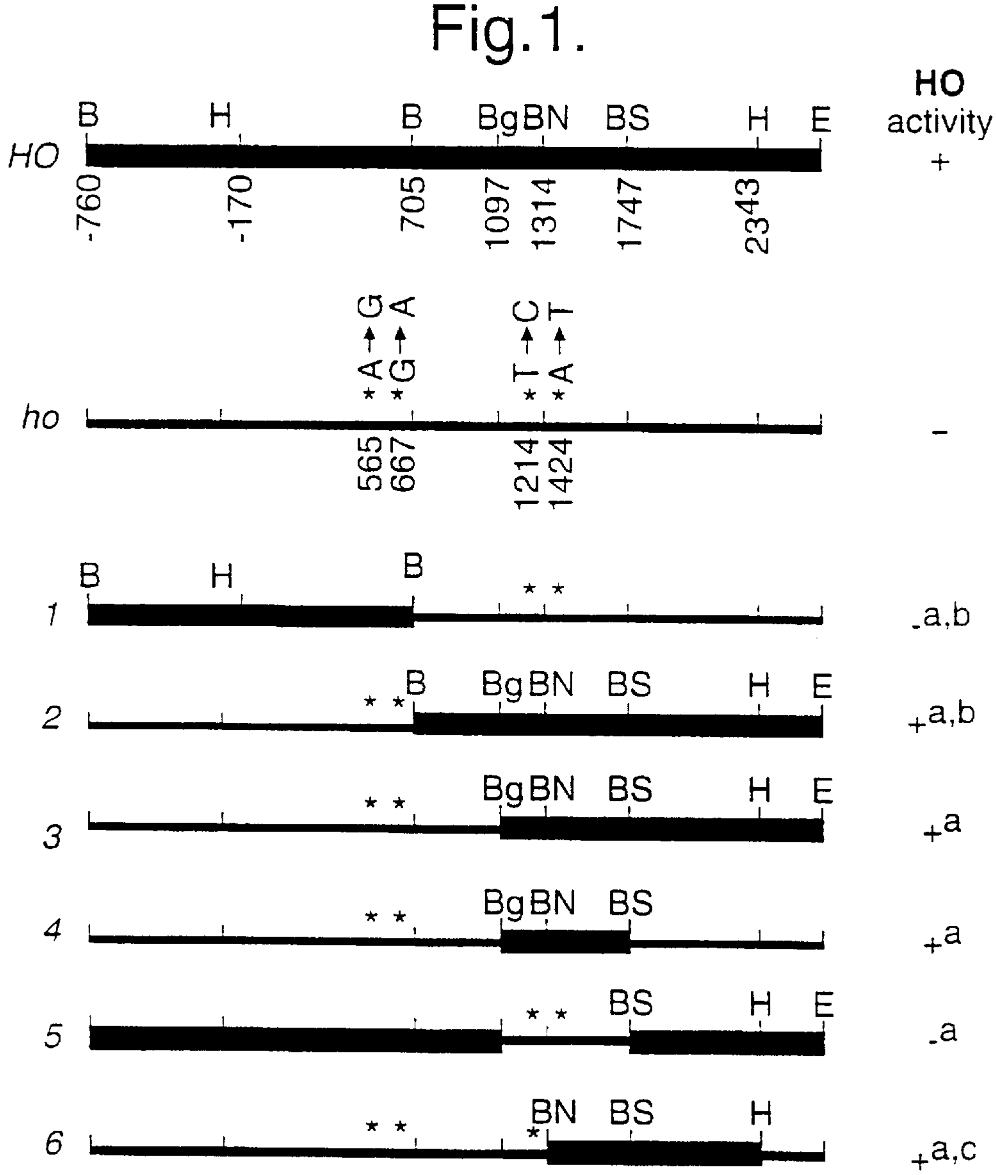

FIG. 1 illustrates partial restriction maps of HO, ho and Ho-ho chimeras of the two genes. The mutations in ho are indicated by asterisks. Chimera 6 shows that by correcting the fourth point mutation to the HO sequence, the activity is restored. This is published in Meiron, et al., ibid., (1995).

Figure 2:
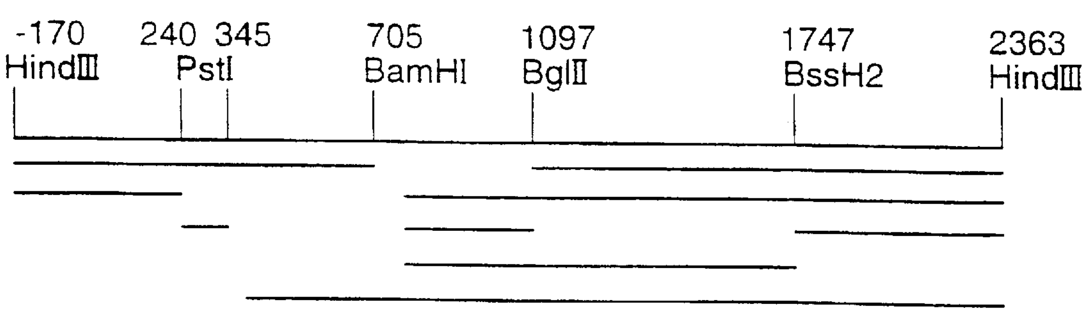

FIG. 2 is an illustration of a sequenced 2.5 kb HindIII fragment of ho [published in Meiron, et al., ibid., (1995)].

Figure 3:
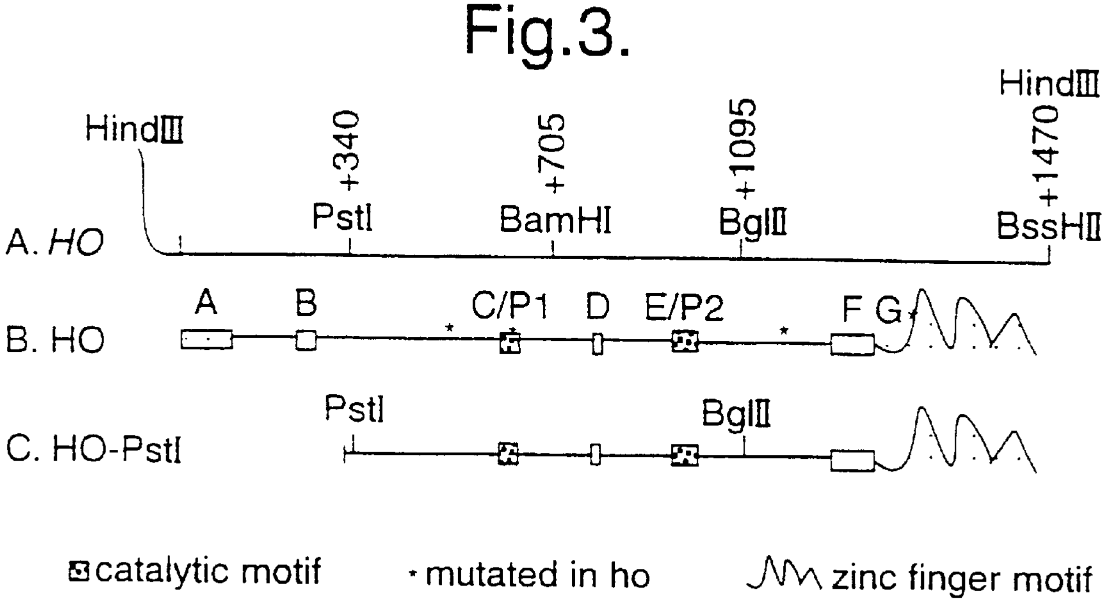

FIG. 3 diagrams the truncations of HO:

FIG. 3*a* illustrates a HO gene with relevant restriction sites within flanking HindIII sites. The Pst1 site at position +345 and the BamH1 site at position +705 are the new N-termini of the truncated proteins. The Bg/2 site at position +1095 and the BssH2 site downstream of the coding region at position +1470 were used for constructing the active genes by gene conversion with the parallel HO gene fragment in Δho yeast cells. The Swi5 zinc fingers were inserted at the above Bg/2 site to make the Ho-Swi5 chimera.

FIG. 3*b* illustrates HO showing two LAGLI-DADG (SEQ ID NO:1) catalytic motifs and zinc fingers. The four point mutations in ho are indicated [*]. The mutation in the zinc finger gives the inactive phenotype.

FIG. 3*c* illustrates that HO Pst1-HindIII retains both catalytic motifs. The catalytic fragment extends from the Pst1 site at position +340 to the Bg/2 site at position +1095.

Figure 4A:
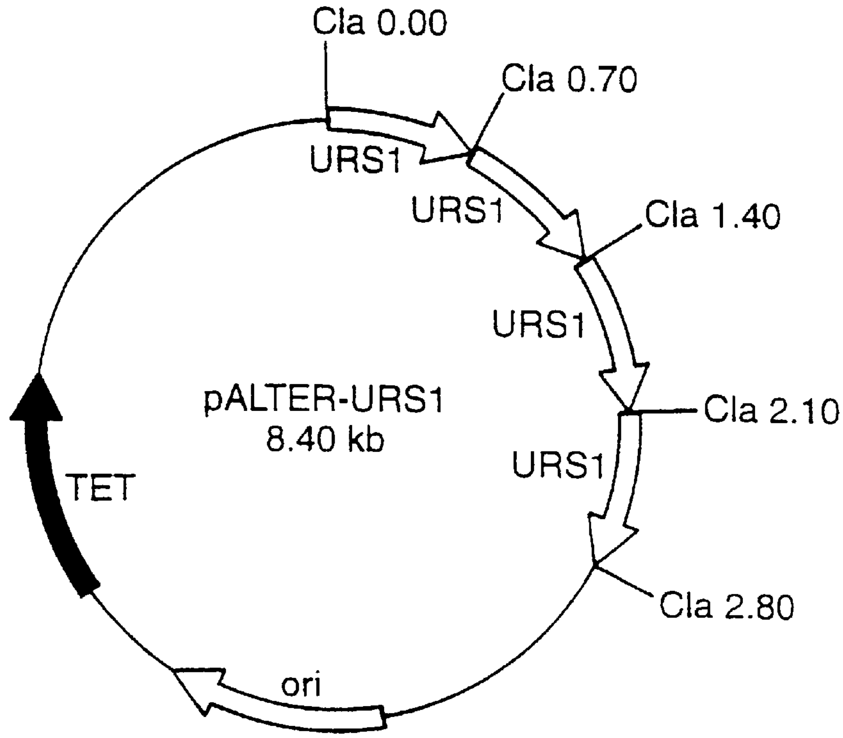

FIG. 4*a* depicts a pALTER-URS1 plasmid used for assaying activity of the Ho-Swi5 chimera. Four repeats of a 700 bp Cla1 URS1 fragment were cloned into pALTER (Promega Co.). A control plasmid consists of pALTER without the Swi5 URS1 DNA binding sequence.

Figure 4B:
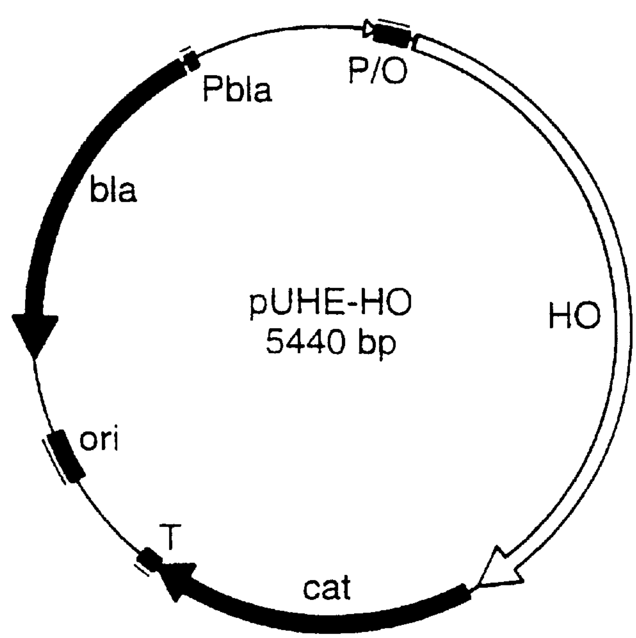

FIG. 4*b* illustrates pUHE-HO, a clone used for making truncations of HO.

Figure 5:
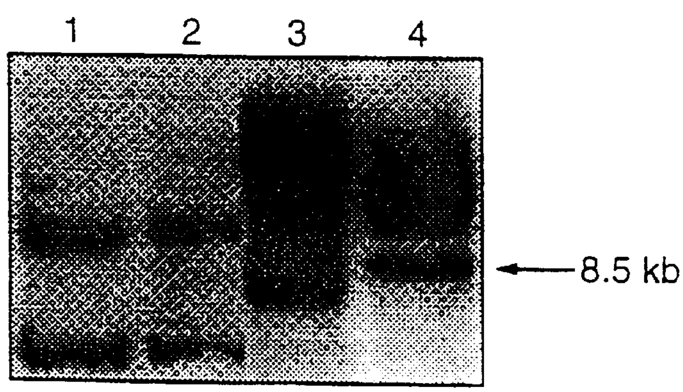

FIG. 5 shows IPTG-induction of the Ho-Swi5 chimera in the bacteria UT5600, in the presence of the pALTER-URS1 assay plasmid and the pALTER control plasmid. The Southern blot was probed with a labelled URS1 fragment.

Lane 1: p-ALTER assay plasmid, Ho-Swi5 chimera induced.

Lane 2: p-ALTER assay plasmid, Ho-Swi5 chimera not induced.

Lane 3: p-ALTER-URS1 assay plasmid, Ho-Swi5 chimera not induced.

Lane 4: p-ALTER-URS1 assay plasmid, Ho-Swi5 chimera induced.

FIG. 6 illustrates primers used for making the Ho-Swi5 chimeric endonuclease:

FIG. 6*a* shows Swi5 finger primers (SEQ ID NOS:2 and 3).

FIG. 6*b* shows primers (SEQ ID NOS:4 and 5) used for subcloning the Ho-Swi5 chimeric endonuclease into the histidine-tagged bacterial vector and into the yeast expression vector.

DESCRIPTION OF PREFERRED EMBODIMENTS

The present invention relates to the characterization of DNA segments encoding the catalytic and DNA-binding domains of HO-endonuclease. In the experiments relating to the present invention, it was discovered that a 755 nt DNA fragment extending from position 340 from the first codon to position 1095 encodes the catalytic domain and a 360 nt DNA fragment starting at position 1095 encodes the DNA recognition/binding domain. It was further found that it is possible to use the nuclease domain in the generation of chimeric restriction enzymes by linking the nuclease domain of HO-endonuclease to a recognition moiety of a different DNA binding protein or to a synthetic polypeptide designed to recognize a specific DNA target sequence, for example, a zinc finger polypeptide. Given that HO is a member of the dodecapeptide family of endonucleases, all of which have an evolutionarily conserved catalytic motif, the present invention relates to the use of the catalytic domain of any member of this enzyme family as an effector domain in the generation of targeted endonucleases.

DNA segments of the present invention can be readily isolated from a biological sample, using methods known in the art such as polymerase chain reaction (PCR) or standard cloning techniques.

The DNA segments of the present invention can be used to generate chimeric restriction endonucleases, by linking other DNA binding protein domains with the catalytic domain of HO. This can be achieved chemically, as well as by recombinant DNA technology. Such chimeric endonucleases are useful for physical mapping and sequencing of genomes of any species such as, for example, humans, mice and plants.

Such chimeric endonucleases are also valuable research tools in recombinant DNA technology and molecular biology. Currently, only 4–6 base pair cutters and about 8 rare cutters are available commercially. By linking other DNA binding proteins to the nuclease domain of HO-endonuclease, or of any other dodecapeptide endonuclease, chimeric endonucleases that recognize specific DNA sequences, both in vivo and in vitro, can be generated.

According to a further embodiment, the present invention relates to a DNA construct and the chimeric endonuclease encoded therein. The DNA construct of the present invention comprises a DNA segment encoding the nuclease domain of HO-endonuclease or of any other dodecapeptide endonuclease, a second DNA segment encoding a DNA binding moiety, and a vector. The two DNA segments are linked to the vector so that expression of the segments can be effected, thereby yielding a chimeric restriction endonuclease. Vectors for expression in prokaryote and eukaryote cells can be used to achieve expression after transformation of the appropriate host cells/organisms. The chimeric endonuclease can either be purified for use as a protein fraction or expressed so as to perform its function within the transformed host cells.

Suitable recognition domains include, but are not limited to, zinc finger motifs, viral replication proteins, homeo domain motifs, DNA binding moieties of gene transcription factors, repressors, oncogenes, and other naturally occurring and synthetic sequence-specific DNA binding proteins that recognize more than 6 base pairs.

The hybrid restriction enzymes of the present invention can be produced by those skilled in the art, using known methodology. For example, the enzymes can be produced using recombinant DNA technology. The chimeric enzymes of the present invention can be produced by culturing commercially available bacterial, yeast, animal or plant cells containing the DNA construct of the present invention and isolating the protein.

While HO-endonuclease is the enzyme studied in the following examples, it is expected that other dodecapeptide endonucleases will function using a similar two-domain structure, which one skilled in the art could readily determine, based on the present invention.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Materials and Method

The following materials and method were utilized in the isolation and characterization of HO-endonuclease functional domains, as exemplified below:

| Bacterial Strains | |
|---|---|
| JM109 | F'traD36 $lacI^q$A{lacZ}M15 $proA^+B^+$le14$^-${McrA$^-$}D{lac-proAB} thi gyrA96{$NaI^r$} endA1 hsdR17 {$r_k^-m_k^+$} relA1 sup E44 recA1 |
| TB1 | F araΔ{lac-proAB} rpsL {$Str^r$}{080dlacΔ{lacZ}{M15}hsdR {$r_k^-m_k^+$} |
| UT5600 | F ara-14 leuB6 azi-6 kacYl proCl4 tsx-67 Δ{ompT-fepC}266 entA403 trpE38 rfbD1 rpsL109 xyl-5 mtl-1 thi-1 |

Yeast Strains

| Name | Genotype |
|---|---|
| 294 | MATα, ho, his3, leu2, trp1, ura3–52 |
| 657 | MATa , ho, lys2, ura3, leu2–3,112, his 3–11, trp1-1, ade2-1 his4::HIS3 4 |
| 657STE6-lacZ | As 657 but with the URA3 gene restored and STE6-lacZ integrated adjacent to it |
| YP52 | MATa, ho, ade2-101, ura3::XHOI (StuI), his3-200, trp1 Δ901, lys2–101 |
| 719 | MATa ho ade1–2 |
| JKM120 | Δho*MATa ade1 leu2–3,112 lys5 trp1::hisG ura3–52 |

*The HO deletion was made by blunt end ligation of the BamH1 site at position +705, with the Sac1 site upstream of the promoter sequences, and removes about 2.2 kb of HO [J. K. Moore and J. E. Haber, personal communication].

Bacterial Expression Vectors

The pUH expression vector pUHE21, which has the T7 promoter $A_1$ and confers ampicillin resistance, was used throughout [M. Lanzer and H. Bujard, "Promoters Largely Determine the Efficiency of Repressor Action," *Proc. Natl. Acad. Sci. USA,* Vol. 85, pp. 8973–8977 (1988)]. HO expression was induced with 20 mM isopropyl β-D-thio-glucopyranoside (IPTG). DNA was extracted from bacteria [Maniatis, et al., *Molecular Cloning: A Laboratory Manual,* Cold Spring Harbor Laboratory Press, Cold Spring Harbor, N.Y., U.S.A.(1982)].

Yeast Expression Vectors and Transformation

Truncated HO proteins were expressed from the GAL1–10 promoter in centromeric plasmids with the URA3 selective marker. Transformations were done with LiAcetate [Ito, et al., *J. Bacteriol.,* Vol. 153, pp. 163–168 (1983)]. Yeast growth media and DNA extraction were as known in the art [Sherman, et al., *Methods in Yeast Genetics,* Cold Spring Harbor Laboraotry Press, Cold Spring Harbor, N.Y., U.S.A. (1986)]. High efficiency yeast transformations were achieved by the protocol of Burgers and Percival [P. M. Burgers and K. J. Percival, "Transformation of Yeast Spheroplasts without Cell Fusion," *Anal. Biochem.,* Vol. 163, pp. 391–397 (1987)].

An *E. coli* β-galactosidase gene expressed off the a-specific STE6 promoter [K. L. Wilson and I. Herskowitz, *Proc. Natl. Acad. Sci. USA,* Vol. 83, pp. 2536–2540 (1986)] was transformed into strain 657. It was targeted [Orr-Weaver, et al., *Methods Enzymol.,* Vol. 101, pp. 228–245 (1983)] with a cut URA3 gene to the ura3 site, where it became integrated adjacent to this gene.

Gene Conversion of the Genomic ho Allele to Generate Chimeric HO/ho Genes

The BamH1-EcoR1 fragment of HO in YCp50,YCp50-HO [R. E. Jensen, et al.,*Proc. Natl. Acad. Sci. USA,* Vol. 80, pp. 3035–3039 (1983)] served as the source of HO fragments. A partial restriction map of the gene is presented in FIG. 1 [D. W. Russell, et al., *Mol. Cell. Biol.,* Vol. 6, pp. 4281–4294 (1986)].

Cloning of the ho Gene by Gap Repair

A retriever vector with HO flanking sequences was prepared from YCp50-HO by removal of the internal 2.5 Kb HindIII fragment. The gapped vector was transformed into the heterothallic yeast strain 294 and plasmids of the appropriate size were chosen for partial sequencing of the ho gene.

Sequencing of the ho Gene ho clones in PUC118 were sequenced by the method of Sanger and Coulson [*Proc. Natl. Acad. Sci. USA,* Vol. 74, pp. 5463–5467 (1977)], using a Sequenase® Version 2.0 kit (USB) and M13 primers.

Construction of HO/ho Chimeric Genes in Vivo

Most chimeric genes were constructed in vivo by transforming heterothallic cells with parts of the HO gene cloned into plasmids, or as fragments cotransformed with a marker plasmid. The resulting chimeric HO-ho genes are indicated as 1–6 in FIG. 1. The BamH1 (−760) to BamH1 (+705) HO fragment (chimera 1) and the reciprocal BamH1 (+705) to EcoR1 (+2760) (chimera 2) were cloned in YCp111 [R. D. Gietz and A. Sugino, *Gene,* Vol. 74, pp. 527–534 (1988)]; the Bg/II (+1097) to EcoR1 (+2760) HO fragment (chimera 3) was cloned in YEp195 [Gietz and Sugino, ibid.]. These plasmids were transformed into heterothallic yeast strains 294 and 657.

The same HO fragments were integrated into the genomic ho allele by cotransformation with YEp195. In addition, the BstNI (+1314) to HindIII (+2363) HO fragment that covers mutation 4 only, was cotransformed into strains 657 and AP34 (chimera 6).

Construction of HO-ho Chimeric Genes in Vitro for Transformation into Yeast

Chimeric HO-ho genes were constructed in vitro and used for transformation of heterothallic strain YP52. The Bg/II (+1097) to BssHII (+1747) fragment of HO (chimera 4) was embedded in the HindIII fragment of ho. The reciprocal construct, the Bg/II-BssHII fragment of ho embedded within the HindIII fragment of HO (chimera 5), was also made. Chimeric HO-ho genes were also constructed in vivo [H. Ma, et al., *Gene,* Vol. 58, pp. 201–216 (1987)] by cotransformation of the BstN1 (+1314) to HindIII (+2363) fragment of HO with YEp-ho of the present invention, cut at the internal BssHII site at position +1747 (chimera 6). The reconstructed chimeric endonuclease gene was assayed for its HO activity in vivo. YCp50-GAL—HO was used to obtain regulated expression of HO endonuclease.

Assays for HO Activity in Yeast Cells a) Mating Test

Restoration of HO activity results in a mating type switch. heterothallic MATa cells were transformed with the HO gene or fragments thereof, as described above. A number of transformed colonies were grown overnight in YePD and aliquots were mixed with the MATa tester strain 719 and the MATα strain 294, and plated on minimal medium plates.

b) Extinction of the Activity of a Resorter Gene Fused to a Specific Promoter

The STE6-lacZ fusion was integrated into the genome of strain 657 at URA3. Restoration of HO activity to MATa cells leads to a switch to α and to the extinction of expression of a-specific genes by the MATα2 repressor protein. The STE6 promoter is also not active in any diploid cells which might arise after some of the cells switch mating type and mate with remaining cells of the original mating type. Transformed colonies were grown overnight in YePD and lysates were prepared for assay of β-galactosidase activity, according to the protocol of Miller [J. H. Miller, *Experiments in Molecular Genetics,* Cold Spring Harbor Laboratory Press, Cold Spring Harbor, N.Y., U.S.A. (1972)].

c) Removal of a Suppressor Gene from the Genome

A suppressor gene was removed from the genome with resulting expression of an ochre canavanine resistant phenotype and an ochre adenine auxotrophy. A heterothallic strain of yeast (AP34) was obtained from M. Kupiec, which strain has an integrated Ty element containing a MAT fragment with the HO-endonuclease recognition site. The MAT gene was deleted in this strain. Downstream of the HO-endonuclease target site within the Ty element is a SUP4° gene. The AP34 strain cells contain the can1–100° and ade2-1° alleles. Introduction of a double strand break into the Ty by HO leads to its excision from the genome, together with the SUP4° gene, resulting in expression of $Can^r$Ade papillae [A. Parket, et al., *Genetics* (1995)]. The appearance of canavanine resistance and adenine auxotrophy were used as an HO assay for gene conversion of the genomic ho allele to an active chimeric gene by fragments of the HO gene. In control experiments, HO was expressed off the GAL promoter from plasmid YCp50-GAL—HO [Jensen, et. al., *Proc. Natl. Acad. Sci. USA,* Vol. 80, pp. 3035–3039 (1983)].

Construction of a Chimeric Endonuclease between the Catalytic Fragment of HO and the Zinc Finger DNA-Binding Domain of the Yeast Transcription Factor Swi5

The HO-Swi5 chimeric endonuclease was constructed by cleaving the Pst1-HindIII fragment of HO in pUHE 300 bps upstream of the first presumptive zinc finger at the Bg12 site (FIG. 2) and ligating in its stead a PCR fragment amplified from plasmid pET13a-m30FST that encodes the three zinc fingers of Swi5 and 30 amino acids upstream of them [R. N. Dutnall, et al., "The Solution Structure of the First Zinc Finger Domain of SW15: A Novel Structural Extension to a Common Fold," *Structure,* Vol. 4, pp. 599–611 (1996)].

HO-Swi5 Chimeric Endonuclease Substrate Plasmid for Activity Assay

For an assay plasmid, there were ligated four copies of a 700-nt Cla1 fragment encoding URS1 of HO, the binding site of Swi5, into pALTER (Promega Co.), a plasmid with the tetracycline marker gene (pALTER-URS1). The two plasmids were cotransformed into strain UT5600 and selected with both ampicillin and tetracycline. Control cultures were transformed with the plasmid encoding the HO-Swi5 chimera and pALTER to test for site-specificity of the cleavage. Overnight cultures were diluted 1:100 and induced at $OD_{600}$ 0.5 with 20 mM IPTG.

Assay of Activity of HO-Swi5 Chimeric Endonuclease

Cells were collected after 24 hour induction and DNA prepared according to the protocol of Colleaux, et al. [L. Colleaux, et al., "Universal Code Equivalent of a Yeast Mitochondrial Intron Reading Frame Is Expressed into *E. coli* as a Specific Double Strand Endonuclease," *Cell,* Vol. 44, pp. 521–533 (1986)]. In parallel, DNA was prepared from non-induced cultures harvested after overnight growth.

The assay plasmid, pALTER-URS1 (FIG. 3), was digested with Cla1 to produce marker bands for the predicted cleavage products that could be produced by the HO-Swi5 chimeric endonuclease. The DNAs were run on 0.7% agarose gels and the Southern blots were probed with a $P^{32}$-dCTP-endlabelled 700 bp Cla1 URS1 DNA fragment [Maniatis, et al., ibid.].

Subcloning of the HO-Swi5 Chimera into a His-Tagged Vector pRSET (Invitrogen) for One Step Purification of the Endonuclease by Metal-Resin Affinity Column A 113-residue N-terminal truncation of HO fused to the zinc finger domain of Swi5 (HO-Swi5 chimeric endonuclease) was subcloned into pRSET (Invitrogen) and transformed into TB1 *E. coli* bacteria. After heat induction of expression, the bacteria were lysed and the lysate passed over a metal-resin affinity column (Qiagen) according to the manufacturer's instructions. An aliquot of the column eluate was run on SDS/PAGE protein gels.

SDS/Page

Proteins were prepared in sample buffer and electrophoresed in SDS (0.1%) polyacrylamide (10%), as known in the art [Laemmli, *Nature,* Vol. 222, pp. 680–685 (1970)]. Proteins were stained with Coomassie blue.

Example 1

Cloning of HO, ho and HO-ho Chimeric Genes into High Expression Bacterial Vectors To delineate residues of HO important for site-specific endonucleolytic activity, the HO gene was cloned into the high expression bacterial vector pUHE. As these experiments are notoriously difficult, the ho gene and a HO-ho chimeric gene that has the inactivating zinc finger mutation were cloned as controls for the ligation and transformation procedures.

HO, ho and HO-ho chimeric genes were cloned in plasmid pUHE and transformed into the above bacterial host strains. Active forms of HO gave no transformants in JM109; only ho and the HO-ho chimeric genes with the zinc finger mutation gave transformants in this $recA^-$strain. Therefore, plasmids encoding an active form of HO were routinely transformed into $recA^+$hosts, strains TB1 and UT5600, as were ho and HO-ho chimeric genes that served as experimental controls.

Example 2

Induction of HO, ho and HO-ho Chimeric Genes in Bacteria

Upon IPTG induction, TB1 cells that were host to active forms of HO showed a reduction in OD after 30 minutes. Cells expressing ho or chimeric HO-ho genes with the zinc finger mutation did not lyse, indicating that bacterial lysis is correllated with HO activity (FIG. 4*a*). This means that TB1 *E. coli* cells can be used to determine endonucleolytic activity of the cloned gene.

Example 3

Delineation of the Minimal Active Fragment of HO that Retains Site Specific Endonucleolytic Activity Two N-terminal truncations of HO were made. In the first, an HO fragment starting from the Pst1 site at position +345 was subcloned into pUHE21; this 113 N-terminal truncation leaves both dodecapeptide catalytic motifs and the C-terminal zinc finger domain intact. The second truncation started at the BamH1 site at position +705 of HO and deleted 236 residues, leaving only 351 C-terminal residues of HO with a single catalytic motif and the C-terminal zinc finger domain (FIG. 2). These subclones were tested for their ability to cause lysis of TB1 cells. A +1-frameshift version of the Pst1-HindIII HO clone was made and served as a control in these experiments.

The 113 N-terminal truncated HO protein induced lysis of the bacteria after 30 minutes of induction. In contrast, the bacteria expressing the 236 residue truncation continued to grow in the presence of IPTG for one hour. The frameshift version of the 113 N-terminal truncation of HO protein that produces a nonsense protein does not cause TB1 bacteria to lyse.

Example 4

Selection of a Bacterial Host Cell for Producing HO Endonuclease and Chimeras Derived from It That Have Site-Specific Endonucleolytic Activity The strain TB1 is derived from JM83 and has an endogenous phage Ø80 that could be responsible for lysis of the bacterial host as a result of a double strand break in the genome made by HO-endonuclease or a chimeric endonuclease. To select bacteria that would not lyse on induction of endonucleolytic activity, the complete HO gene and the 113-residue HO truncation were transformed into strain UT5600, that has no endogenous bacteriophage. When the cells were induced with IPTG, there was no lysis. This was not due to inactivation of the promoter from which HO was being expressed, as the same plasmids isolated from the UT5600 cells and transformed into fresh TB1 cells gave rise to lysis after IPTG induction.

Example 5

Correlation of Bacterial Lysis with the Ability of the Truncated HO Protein to Initiate a Mating type Switch in Yeast Site specificity of the cleavage was assayed by initiation of a mating type switch in yeast. When the above HO fragments were subcloned into yeast vectors for expression from the GAL1 promoter, there were no transformants in $recA^-$ strains and consistent plasmid rearrangements in $recA^+$ bacteria. Therefore, HO-truncated proteins were constructed, expressed from the GAL1 promoter by gap repair in yeast from two fragments. The Pst1-Bg/2 fragment of HO lacking the zinc finger domain was cloned downstream of the GAL1 promoter of YCp16F [P. K. Foreman and R. W. Davis, "Cloning Vectors for the Synthesis of Epitope-Tagged, Truncated and Chimeric Proteins in *Saccharomyces cerevisiae,*" *Gene,* Vol. 144, pp. 63–68 (1994)]. It was cleaved at the BamH1 site and cotransformed into yeast with a Pst1-HindIII fragment of HO. The restriction sites are illustrated in FIG. 2. Similarly, the BamH1HindIII ho fragment was cloned downstream of the GAL1 promoter of YCpGAL [Jensen, ibid. (1983)], cleaved with BssHII downstream of the zinc finger domain and cotransformed into yeast with the BamH1-HindIII fragment of HO. The host yeast strain, JKM120, is MATa and the ho gene is deleted to the BamH1 site, as is the 236-residue truncation. This precludes any possibility of activation of the genomic ho gene by gene conversion from the transforming HO fragment. $Ura^+$ transformants were induced in YEP medium [F. Sherman, *Methods in Yeast Genetics,* Cold Spring Harbor Laboratory Press, Cold Spring Harbor, N.Y., U.S.A. (1986)] containing 2% galactose for 24 hours and plated with the MATa mating tester strain 719, to test for a mating type switch. Only the 113-residue truncated HO protein was capable of inducing a mating type switch in yeast. Rare matings obtained on minimal SD plates [F. Sherman, ibid.] between $Ura^+$ transformants containing the 236 residue truncation of HO were not capable of continued growth on minimal SD plates and gave rise to abnormal tetrads on sporulation plates.

Example 6

Cleavage of the URS1 Plasmid by the HO-Swi5 Chimeric Endonuclease

UT5600 bacterial cells containing both the HO-Swi5 expression plasmid, pUHE and the URS1 assay plasmid and induced with IPTG showed a linearized band in Southern blots probed with an URS1 probe. The strongest band is at 8.5 kb and corresponds to the linearized URS1 plasmid and represents a single cleavage by the HO-Swi5 chimeric endonuclease. These bands were strongest after overnight induction (FIG. 5).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

---

What is claimed is:

1. An isolated DNA segment encoding a domain of HO-endonuclease, said segment being selected from the group consisting of:

a) an isolated DNA segment encoding the N-terminus of HO-endonuclease which contains the sequence-specific catalytic nuclease activity of said HO-endonuclease, said DNA fragment comprising at least 755 nucleotides (nt) and encoding for at least 251 amino acids, and said endonuclease being characterized by the presence of at least one copy of the dodecapeptide motif LAGLI-DADG (SEQ ID NO:1) ; and b) an isolated DNA segment encoding the C-terminus of HO-endonuclease which contains the DNA binding/recognition activity of said HO-endonuclease, said C-terminus comprising 360 nt and encoding for 120 amino acids.

2. An isolated DNA segment according to claim 1, encoding the N-terminus of HO-endonuclease which contains the sequence-specific catalytic nuclease activity of said HO-endonuclease, said DNA segment comprising 755 nt and encoding for 251 amino acids.

3. An isolated DNA segment according to claim 2, wherein said N-terminal, 755 nt DNA segment extends from position 340 to position 1095.

4. An isolated DNA segment according to claim 1, encoding the C-terminus of HO-endonuclease which contains the DNA binding/recognition activity of said HO-endonuclease, said C-terminus comprising 360 nt and encoding for 120 amino acids.

5. An isolated DNA segment according to claim 4, wherein said C-terminal, 360 nt DNA segment starts at position 1095 and encodes a 13.5 kDa protein segment comprising the DNA binding/recognition domain.

6. A DNA construct, comprising:

a DNA segment encoding the catalytic nuclease domain of a dodecapeptide endonuclease; and a second DNA segment encoding a DNA binding moiety and a vector, said endonuclease being characterized by the presence of at least one copy of the dodecapeptide motif LAGLI-DADG (SEQ ID NO:1).

7. A DNA construct according to claim 6, wherein said endonuclease is characterized by the presence of two copies of the dodecapeptide motif LAGLI-DADG (SEQ ID NO:1).

8. A DNA construct according to claim 6, wherein said dodecapeptide endonuclease is HO-endonuclease.

9. A chimeric restriction endonuclease, comprising:

the catalytic nuclease domain of a dodecapeptide endonuclease linked to a recognition domain of a different DNA binding protein;

said endonuclease being characterized by the presence of at least one copy of the dodecapeptide motif LAGLI-DADG (SEQ ID NO:1).

10. A chimeric restriction endonuclease as claimed in claim 9, comprising the catalytic nuclease domain of HO-endonuclease, linked to a recognition domain of a different DNA binding protein.

11. A chimeric restriction endonuclease as claimed in claim 9, wherein said catalytic nuclease domain is linked to a recognition domain of a sequence-specific DNA binding protein which recognizes>6 base pairs.

12. A chimeric restriction endonuclease as claimed in claim 9, wherein said recognition domain is selected from the group consisting of a zinc finger motif, a viral replication protein, a homeodomain motif, a DNA binding moiety of a gene transcription factor, a repressor, and a DNA binding moiety of an oncogene.

13. A chimeric restriction endonuclease as claimed in claim 9, comprising the catalytic nuclease domain of HO-endonuclease linked to a synthetic polypeptide designed to recognize a specific DNA target sequence.

14. A chimeric restriction endonuclease as claimed in claim 13, wherein said polypeptide is a zinc finger polypeptide.

15. A chimeric restriction endonuclease as claimed in claim 13, wherein said DNA target sequence is an oligonucleotide.

16. A method of forming a chimeric restriction endonuclease, comprising linking a DNA segment encoding a catalytic nuclease domain of a dodecapeptide endonuclease and a DNA segment encoding a recognition domain of a different DNA binding protein, said catalytic nuclease domain being characterized by the presence of at least one copy of the dodecapeptide motif LAGLI-DADG (SEQ ID NO:1); and expressing the linked DNA segments to produce the chimeric restriction endonuclease.

* * * * *

```
SEQUENCE LISTING

(1) GENERAL INFORMATION:

   (iii) NUMBER OF SEQUENCES: 5

(2) INFORMATION FOR SEQ ID NO:1:

     (i) SEQUENCE CHARACTERISTICS:
          (A) LENGTH: 9 amino acids
          (B) TYPE: amino acid
          (C) STRANDEDNESS:
          (D) TOPOLOGY: linear

    (ii) MOLECULE TYPE: peptide

    (ix) FEATURE:
          (A) NAME/KEY: Peptide
          (B) LOCATION: 1..9
          (D) OTHER INFORMATION: /note= "endonuclease dodecapeptide
```

-continued motif"

(xi) SEQUENCE DESCRIPTION: SEQ ID NO:1:

Leu Ala Gly Leu Ile Asp Ala Asp Gly
1 5

(2) INFORMATION FOR SEQ ID NO:2:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..29
(D) OTHER INFORMATION: /note= "NDEFWRD Bam site SWI5 zinc finger primer"

(xi) SEQUENCE DESCRIPTION: SEQ ID NO:2:

ATGACAAATG GATCCTCAAA AATCACAAG 29

(2) INFORMATION FOR SEQ ID NO:3:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..28
(D) OTHER INFORMATION: /note= "NDEREV Hind3 site SWI5 zinc finger primer"

(xi) SEQUENCE DESCRIPTION: SEQ ID NO:3:

CCGCTGCAAA GCTTTCCTAC TTCTGTGC 28

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..30
(D) OTHER INFORMATION: /note= "HOSWF Nde site HO-SWI5 chimera primer"

(xi) SEQUENCE DESCRIPTION: SEQ ID NO:4:

CTGCAGCAAT GTCATATGCT TGATGGTAGG 30

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: single
(D) TOPOLOGY: linear -continued

```
    (ii) MOLECULE TYPE: DNA

    (ix) FEATURE:
          (A) NAME/KEY: -
          (B) LOCATION: 1..30
          (D) OTHER INFORMATION: /note= "HOSWB Bam site HO-SWI5
               chimera primer"

    (xi) SEQUENCE DESCRIPTION: SEQ ID NO:5:

CGGGATCCGC TGCAAAGCAT TCTACTTCTG                                    30
```